(12) United States Patent
Zeng et al.

(10) Patent No.: US 10,213,095 B2
(45) Date of Patent: Feb. 26, 2019

(54) PERCUTANEOUS PUNCTURE AND DILATION VISIBLE IRRIGATION-SUCTION SYSTEM AND METHOD OF USING THE SAME

(71) Applicants: THE FIRST AFFILIATED HOSPITAL OF GUANGZHOU MEDICAL UNIVERSITY, Guangzhou, Guangdong (CN); HANGZHOU HAWK PHOTOELECTRIC INSTRUMENT CO., LTD., Hangzhou, Zhejiang (CN); GUANGZHOU MINITECH TRADE COMPANY LTD., Guangzhou, Guangdong (CN)

(72) Inventors: Guohua Zeng, Guangdong (CN); Guohua Bao, Zhejiang (CN); Xinrong Lu, Zhejiang (CN); Lifang Hua, Zhejiang (CN); Jianqiang Ma, Guangdong (CN)

(73) Assignees: The First Affiliated Hospital of Guangzhou Medical University, Guangzhou (CN); Hangzhou Hawk Photoelectric Instrument Co., Ltd., Hangzhou (CN); Guangzhou Minitech Trade Company Ltd., Guangzhou (CN)

( * ) Notice: Subject to any disclaimer, the term of this patent is extended or adjusted under 35 U.S.C. 154(b) by 141 days.

(21) Appl. No.: 15/226,890

(22) Filed: Aug. 2, 2016

(65) Prior Publication Data

US 2017/0340191 A1 Nov. 30, 2017

(30) Foreign Application Priority Data

May 26, 2016 (CN) .......................... 2016 1 0357478

(51) Int. Cl.
*A61B 1/00* (2006.01)
*A61B 1/313* (2006.01)
(Continued)

(52) U.S. Cl.
CPC ................ *A61B 1/015* (2013.01); *A61B 1/00* (2013.01); *A61B 1/00119* (2013.01);
(Continued)

(58) Field of Classification Search
CPC ............ A61B 1/00091; A61B 1/00094; A61B 1/00119; A61B 1/00128; A61B 1/00135;
(Continued)

(56) References Cited

U.S. PATENT DOCUMENTS

| 2008/0091061 A1* | 4/2008 | Kumar | ............... | A61B 1/00068 600/104 |
| 2009/0192466 A1* | 7/2009 | Sniffin | ............... | A61B 17/3421 604/167.01 |

* cited by examiner

*Primary Examiner* — Ryan Henderson (57) ABSTRACT

The invention discloses a percutaneous puncture and dilation visible irrigation-suction system and a method of using the same. The system comprises a main tube, which is contiguous with the sheath tube and has an end for an endoscope insertion. The sheath tube comprises an inner sheath and an outer sheath joined together in a sleeve type. There is a space between inner and outer sheath. The inner sheath is connected to main tube, together building a channel via which the endoscope is inserted and withdrawn. The sheath tube is connected to main tube after completing puncture and dilation, then endoscope system is introduced for observation and operation. The present invention provides a percutaneous puncture and dilation visible irrigation-suction system and a method of using the same, with a continuous controllable visible negative pressure aspirator, achieving high irrigation and powerful suction efficiency, as well as clear endoscopic view.

6 Claims, 5 Drawing Sheets

(51) Int. Cl.
  *A61B 1/015* (2006.01)
  *A61B 17/34* (2006.01)
  *A61M 1/00* (2006.01)
  *A61B 1/12* (2006.01)
  *A61B 1/06* (2006.01)

(52) U.S. Cl.
  CPC ...... *A61B 1/00135* (2013.01); *A61B 1/00154* (2013.01); *A61B 1/0661* (2013.01); *A61B 1/12* (2013.01); *A61B 1/3132* (2013.01); *A61B 17/34* (2013.01); *A61B 17/3421* (2013.01); *A61M 1/008* (2013.01); *A61M 1/0058* (2013.01); *A61B 2017/3445* (2013.01); *A61B 2017/3447* (2013.01)

(58) Field of Classification Search
  CPC ............ A61B 1/00142; A61B 1/00154; A61B 1/012; A61B 1/015; A61B 1/018; A61B 1/12; A61B 1/126; A61B 1/127; A61B 1/128; A61B 1/303; A61B 1/307; A61B 17/34; A61B 17/3421; A61B 2017/3445; A61B 2017/3447; A61M 1/008; A61M 1/0084; A61M 1/0086; A61M 1/0058; A61M 1/006; A61M 1/0062; A61M 1/0064
  USPC ............. 604/164.01, 164.02, 164.07, 164, 9, 604/164.11, 164.13, 167.01–167.06
  See application file for complete search history.

PERCUTANEOUS PUNCTURE AND DILATION VISIBLE IRRIGATION-SUCTION SYSTEM AND METHOD OF USING THE SAME

CROSS-REFERENCE TO RELATED APPLICATIONS

The present application claims the benefit of Chinese Patent Application No. 201610357478.9 filed on May 26, 2016, the contents of which are hereby incorporated by reference.

FIELD OF THE INVENTION

The present invention relates to a surgical instrument and a method of using the same, more particularly to a percutaneous puncture and dilation visible irrigation-suction system and a method of using the same.

BACKGROUND OF THE INVENTION

Generally, during the traditional percutaneous endoscopic procedures, such as minimally invasive percutaneous nephrolithotomy, irrigation fluid with a predetermined safe pressure and flow is perfused into intrarenal pelvicaliceal system through the working channel of the endoscopy. The reasons are as follows:

1. Artificially dilating the pelvicaliceal system to expose the surgical area;

2. Washing the surgical area to maintain a clear endoscopic vision;

3. Cleaning the surgical area and clearing the bacteria or endotoxins;

4. Flushing out the substances like fragmented stones by the different pressure between internal and external renal when withdraw the endoscope.

At the beginning of traditional percutaneous endoscopic procedures, such as minimally invasive percutaneous nephrolithotomy, a proper size percutaneous puncture tract should be established at first as needed. Meanwhile, an endoscope matched with the percutaneous puncture tract should also be selected. During the procedure, further percutaneous puncture tract dilation would be carried out, or multiple percutaneous puncture tracts would be used, if needed.

The primary intraoperative complications of traditional percutaneous endoscopic procedures, such as minimally invasive percutaneous nephrolithotomy, are as follows:

1. Sepsis. Although the irrigation pressure and flow could be set within a safe range on the irrigation pump, maintaining low intraoperative intrarenal pressure was mainly achieved by evacuating fluid via the space between the percutaneous puncture access sheath and the endoscope, or by discharging fluid through percutaneous puncture access sheath to external body when withdraw the endoscope. If irrigation pressure beyond the upper limit of predetermined safe parameter persistently, especially when infectious diseases coexist, sepsis will remarkably increase.

2. Residual stones. When the irrigation pressure is lower than intrarenal pressure, the unbalance between irrigation and evacuating fluid would cause unclear in traoperative field visibility, and subsequently the difficulty of procedures would increase, which lead to residual stones or more sessions required.

3. Bleeding.

SUMMARY OF THE INVENTION

The present invention provides a visible percutaneous puncture and dilation irrigation-suction system and a method of using the same, characterized by good versatility, increased irrigation-suction efficiency, clear intraoperative field visibility, a continuous controllable visible negative pressure aspirator and safe intraluminal pressure. The present invention solves existing instrumental and technical problems, including low irrigation pressure, obscured visibility, small irrigation and suction channel, complicated procedures, and poor versatility due to different instruments required by different kinds of procedures.

The present invention is achieved by the technology solutions disclosed below.

A visible percutaneous puncture and dilation irrigation-suction system comprises a main tube, which is contiguous with a sheath tube at one end and has a receptacle for a silicone or rubber sealing cap at the other end, where an endoscope is inserted. A suction tube connects to the main tube. Main tube is connected to sheath tube via sheath body. Besides, an irrigation port is connected to the sheath body. The sheath tube comprises an inner sheath and an outer sheath joined together in a sleeve type. Fluid is pumped into the irrigation port and flows through the space between inner and outer sheaths, and then outflow via the fluid outlet openings at the end of the outer sheath. After main tube is connected with sheath tube, the inner sheath and main tube together build a channel via which the endoscope is placed and withdrawn, or flushed substances are aspirated. Endoscope integrated with the parts mentioned above together form a new irrigation-suction system. This new irrigation-suction system could generate a multiple-channel, multiple-orientation, vortex irrigation fluid and assemble a continuous controllable visible negative pressure aspirator, which are the two primary features. Sheath tube is an integrated double-layer structure composed of an inner and an outer sheath. Traditional irrigation fluid could only flow through the working channel of the endoscope. The space between inner and outer sheath is used as an irrigation channel, which cover the shortage of traditional irrigation. During procedures, sufficient irrigation fluid is supplied into the lumen of the visceral organ in multiple orientations via the irrigation channel by setting a predetermined safe pressure and flow on the irrigation pump. On the other hand, the irrigation and suction procedure could be performed simultaneously. Irrigation fluid is pumped into the irrigation port in the sheath body and flow through the irrigation channel between inner sheath and outer sheath. Moreover, suction procedure is performed by connecting the suction tube, which is connected to the main tube, to the negative pressure aspirator, producing a continuous controllable negative pressure. The irrigation and suction channel are totally independent, achieving a safe and controllable intraluminal pressure. Meanwhile, inserting the endoscope through main tube makes the operative field visible, which enhances the safety and efficiency of the procedure. Of note, both irrigation and suction channel are one-way designed. The space between inner and outer sheath of sheath tube is only used for irrigation, while the suction procedure is carried out through space between the working channel and endoscope. Working channel of the endoscope can only be used for inserting instruments, avoiding lowering the efficiency of suction when the irrigation fluid colliding the postoperative fluid sucked or flushed out via inner sheath channel. The postoperative fluid contains all the substances after intraluminal procedure. The endoscope is placed and withdrawn in the channel of main tube and inner sheath. Outer sheath with ≤30 Fr size and 40-200 mm working length could be selected for procedure. Various sizes of endoscopes are suitable for different operations. Any combination of ≤20 Fr outer diameter and ≤10.5 Fr working channel endoscopes could be selected.

The main tube and sheath tube could be an integrated structure or two separated parts. As separated parts, it is easy to clean and change. Preferably, the main tube and the inner sheath are coaxial. The main tube is connected to sheath tube by a sheath body. The irrigation port is arranged at a junction between the main tube and the sheath tube. The irrigation port can also be connected to the sheath body. The irrigation port can be arranged at beginning end of the sheath tube, therefore, it is convenient to inject fluid to the space between inner and outer sheath of the sheath tube, generating a one-way irrigation channel.

Preferably, the sheath body comprises a sheath main body and a sheath base sleeved on the outer sheath. A guiding conical surface is provided at the joint part between the sheath base and main tube. The main tube is mounted to the guiding conical surface. The sheath main body and the sheath base are fixed by a lock nut. The guiding conical surface facilitates the connection between main tube and inner sheath. Spiral connection with a lock nut between sheath main body and sheath base fixes the main tube to the sheath tube. The whole structure is simple and easily disassembled. It also convenient to clean and sterilize each component.

More preferably, a merging area is designed at the free end of the sheath tube. The merging area is embedded between the inner and outer sheath. Two layers of the sheath tube merge at the merging area. Fluid outlet openings in the free end of sheath tube are designed in the sheath tube merging area. This design ensures the one-way irrigation channel unimpeded. Therefore, fluid outlet openings in the sheath tube merging area allow more irrigation flow.

Preferably, the suction tube is connected to a negative pressure valve and a negative pressure control hole is designed in the suction tube. Once the suction tube is connected to the continuous controllable negative pressure aspirator, the negative pressure could be adjusted by either opening or occluding the pressure control hole. Herein, the negative pressure suction power could be easily and quickly adjusted. When the negative pressure control hole is completely open, the negative pressure suction power from negative pressure control hole to suction tube outlet to outside is not affected. Meanwhile, the power is significantly deceased between the negative pressure control hole and emerging area of sheath tube, but it is still enough to generate negative pressure for suction. When the negative pressure control hole is completely occluded, the negative pressure suction power within the channel from emerging area to the negative pressure control hole is uniform. In this situation, the efficiency of negative pressure suction reaches highest. The postoperative fluid containing all the substances after intraluminal procedure is forced to exit the body in the shortest time.

Preferably, an end of the main tube is designed for inserting the endoscopes. The said end also has a receptacle for a silicone or rubber sealing cap which seals the channel to maintain negative pressure suction.

Preferably, the endoscope comprises an endoscope body, an endoscope tube connected with the endoscope body, and an endoscope sheath which is sleeved on the endoscope tube and is fixedly secured to the endoscope body by a sheath lock. A working channel and an optical channel are provided inside the endoscope tube. The working channel is connected with an instrument inlet provided in the endoscope body. The optical channel is connected with onicular lens provided in the endoscope body. An irrigation port is also designed in the endoscope body. The working channel could be chosen to act as an exclusive channel for instruments, while the irrigation fluid flows through other channels for intraluminal irrigation, so that sufficient irrigation fluid can be provided without any disturbance.

Preferably, two fluid tubes are welded to the external surface of endoscope tube. The two fluid tubes are in parallel with endoscope tube. An irrigation port which is connected to the fluid tube is arranged on the endoscope body. During procedures, if additional irrigation fluid is needed to clear the surgical area, one or two more irrigation channels, which are shared the same channel with the working channel, could be added. The fluid tubes welded to the external lateral surface of endoscope tube, together with the additional channel at the dorsal part of endoscope tube offers, offer additional vortex irrigation fluid during intraluminal procedures. With the two fluid tubes for irrigation, a clearer intraoperative visibility may be obtained and a better surgical outcome may be achieved.

A method of using a percutaneous puncture and dilation visible irrigation-suction system comprises steps as follows:

In the preoperative step, choosing a proper size sheath tube according to different cases.

In the percutaneous puncture and dilation step, placing a proper obturator into the sheath tube firstly, to form a puncture and dilation instrument. Then, performing precise orientation under the guidance of ultrasound, bedside fluoroscopy, or mobile C arm fluoroscopy. After that, selecting 18-gauge needle for puncture into cavity of target organ. Then, introducing guide wire via the needle, making a confirmation with imaging, and then pulling out the needle, thereby establishing a percutaneous puncture tract. After that, removing the obturator, inserting the endoscope system through the endoscopy channel comprised of main tube and inner sheath, checking the puncture depth of distal end of sheath tube on the monitor, if not suitable, then adjustment could be made under fluoroscopic guidance.

In the assembling percutaneous puncture and dilation irrigation-suction system step, firstly connecting and fixing main tube with sheath tube after completion of precise percutaneous puncture and dilation. Then, connecting irrigation port in the sheath body to the irrigation pump with predetermined safe irrigation pressure and flow, connecting sample collection bottle to suction tube, and connecting the suction exit of collection bottle to a continuous negative pressure aspirator.

In the endoscope system working step, connecting the endoscope system to camera light source firstly, and introducing Laser fiber, lithotripter probe or electrode into the working channel in the endoscope system. Then, opening the irrigation port in the sheath body, and turning on the irrigation pump, negative pressure suction aspirator, camera light source and treatment device. After that, inserting endoscope successively through the rubber sealing cap at the end of main tube, main tube and the inner sheath of sheath tube, finally into the cavity of target organ. By real-time occluding and opening the negative pressure control hole in the main tube, a continuous controllable safe negative pressure suction is achieved in the cavity of target organ when continuous safe positive pressure irrigation is carried out at the same time. Due to the difference between intraluminal irrigation pressure and sucking negative pressure, an irrigation-suction effect is generated, comprising multiple-orientation, vortex irrigation fluid and one-way negative pressure suction. The irrigation-suction effect could take away the postoperative fluid containing all the substances after intraluminal procedure quickly and thoroughly.

Finally, at the end of procedure, confirming there is no residual substance with the real-time imaging, withdrawing the endoscope, then placing drainage tube through the guide wire, and removing the percutaneous puncture and dilation irrigation-suction system and guide wire. Then, fixing the drainage tube. The procedure is finished.

In conclusion, a percutaneous puncture and dilation visible irrigation-suction system in the present invention has advantages as follows: Space between inner and outer sheath of sheath tube is used as the irrigation channel. Besides, the inner sheath is used as the channel where endoscope is inserted and withdrawn, as well as negative pressure suction. Therefore, the irrigation and suction channel are separate and one-way channels. This special design avoids irrigation fluid colliding the postoperative fluid sucked or flushed out, thus enhancing the efficiency of suction. In the meanwhile, clear endoscopic view is obtained by endoscope combined with sufficient irrigation fluid, which keeps the procedure going smoothly and increase safety of procedure. On the other hand, suction tube located on main tube maintains continuous negative pressure and thus significantly enhances irrigation-suction efficiency. Moreover, different outer diameter and working length of sheath tube can be selected according to different cases.

DETAILED DESCRIPTION OF ILLUSTRATED EMBODIMENTS

The present invention will be further explained below in detail in conjunction with figures and embodiments.

Figure 1:
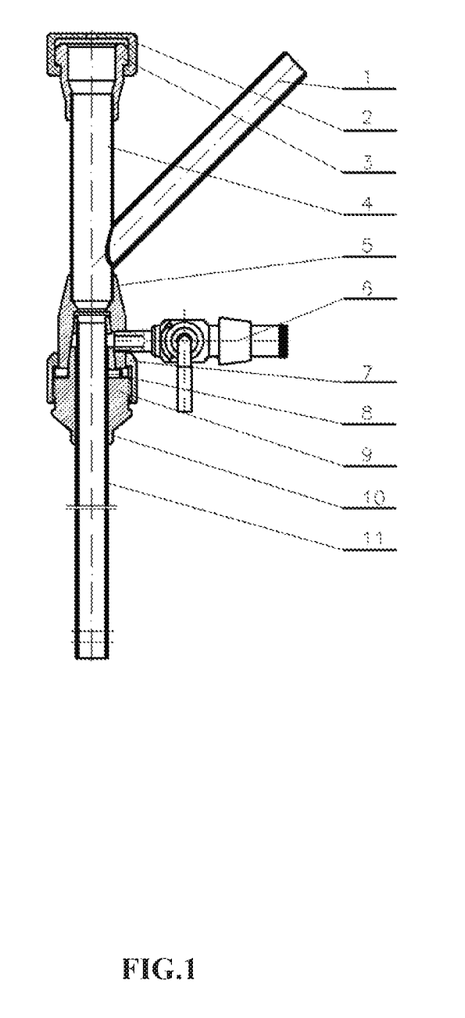
FIG. 1 is a percutaneous puncture and dilation visible irrigation-suction system according to an embodiment of the present invention, without installing an endoscope.
Figure 2:
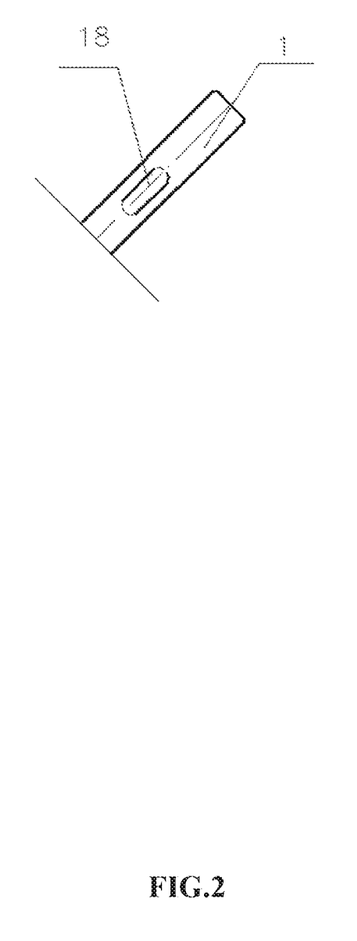
FIG. 2 is an enlarged view of the part A as shown in FIG. 1.
Figure 3:
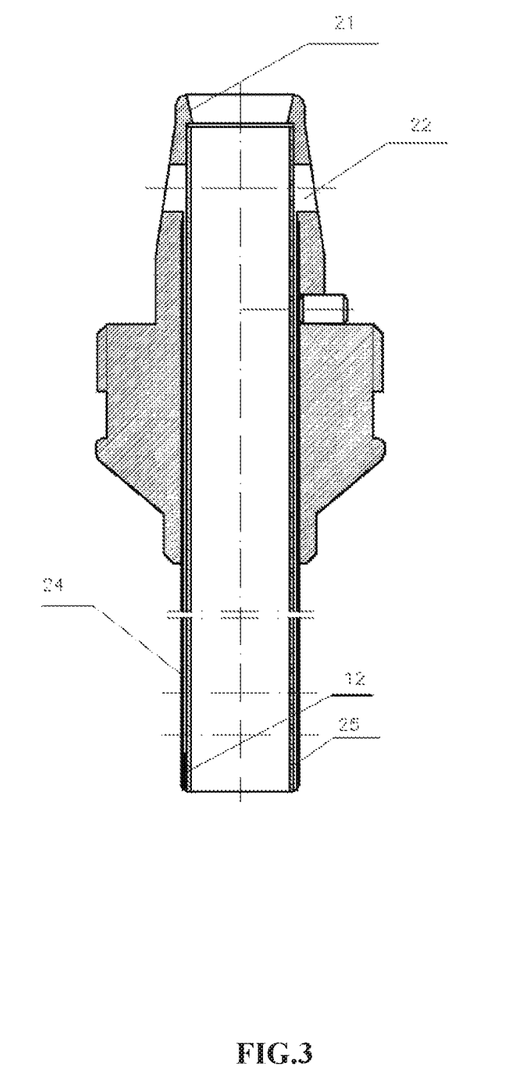
FIG. 3 is an enlarged view of the sheath tube part as shown in FIG. 1.
Figure 4:
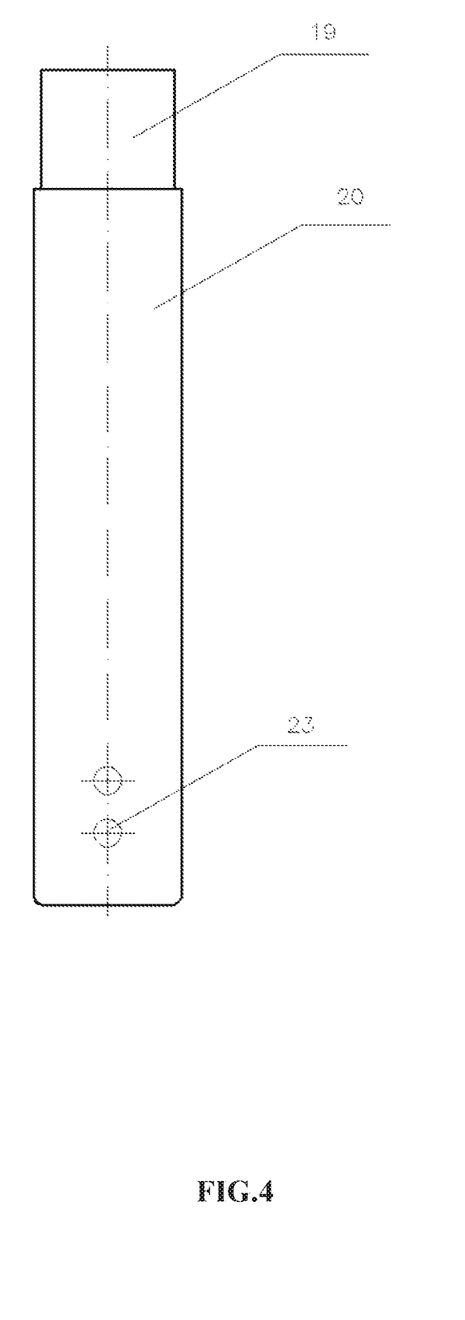
FIG. 4 is a side view illustrating the inner and outer sheaths as shown in FIG. 3 are separated.

Embodiments are as follows:

As shown in FIGS. 1-2, a percutaneous puncture and dilation visible irrigation-suction system comprises a main tube 4 which is arranged with an endoscope inlet at one end. An endoscope inlet port 3 is arranged at the endoscope inlet of the main tube 4, and a rubber sealing cap 2 is covered on the endoscope inlet port 3. Furthermore, a suction tube 1 is provided and is connected to the main tube 4. A negative pressure controllable hole 18 is designed in the suction tube 1. The other end of main tube 4 is contiguous with the sheath tube which comprises an inner sheath 19 and an outer sheath 20 joined together in a sleeve and coaxial type. Main tube 4 and inner sheath 19 are coaxially joined together to establish a common channel for endoscope passage and sucking out the irrigation fluid. The main tube 4 is connected to the sheath tube with sheath body, which comprises sheath main body 5 and sheath base 9. Sheath base 9 is connected to outer sheath 20. Sheath main body 5 is connected to main tube 4. An irrigation port 6 is arranged at a junction between the main tube 4 and the sheath tube. In an optional manner, irrigation port 6 can also be connected to the sheath body, or even to the sheath main body 5. Guiding conical surface 21 is designed at the joint between sheath base 9 and main tube 4. Main tube 4 is installed to the guiding conical surface 21, then sheath main body 5 and sheath base 9 are seamless connected with a positioning pin 8 and then fixed by a lock nut 7. As shown in FIGS. 3-4, the fluid inlet openings 22 are provided on the sheath base 9 sleeved on an upper end of the outer sheath 20 and are connected with the irrigation port 6, and two fluid outlet openings 23 are provided at the other end of the outer sheath 20. The space between inner and outer sheath is used as irrigation channel 24. The fluid outlet openings at the end of outer sheath are used for intraluminal irrigation. A merging area 12 is designed for plugging the space between inner and outer sheath. The merging area 12 is located at the free end of sheath tube. Of note, several fluid outlet openings in the merging area are located at the front end of sheath tube, which increases output quantity of irrigation fluid.

Figure 5:
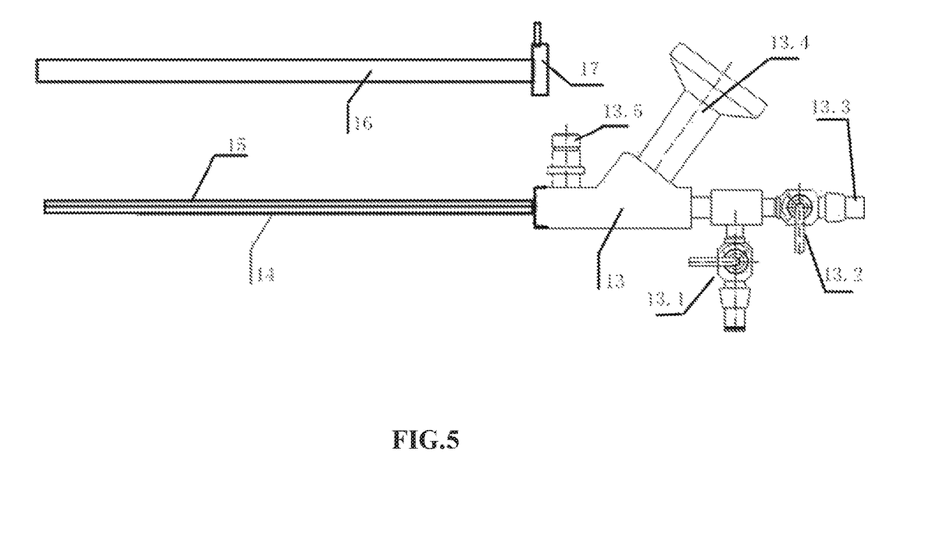
FIG. 5 is a schematic view illustrating an endoscope is disassembled.

As shown in FIG. 5, the composition of an endoscope is as follows: an endoscope body 13, an endoscope tube 14 connected to the endoscope body 13, and an endoscope sheath 16 which is sleeved on the endoscope tube 14. Endoscope sheath is fixedly secured to the endoscope body 13 by a sheath lock 17. A working channel 13.3 and an optical channel are provided inside the endoscope tube 14. The working channel 13.3 is connected with an instrument inlet provided in the endoscope body. The optical channel is connected with an onicular lens group 13.4 provided in the endoscope body and is arranged with optical components, such as object lens, at the front end. An irrigation port 13.2 of the endoscope is connected to endoscope body 13. In order to replenish irrigation fluid, a fluid tube 15 can be welded to the external surface of the endoscope tube. The fluid tube 15 is in parallel with endoscope tube. The replenishing-irrigation port 13.1 which is connected to the fluid tube 15 is designed in the endoscope body 13. The endoscope body is further installed with a light transmitting bundle inlet port 13.5 for introducing light transmitting bundle into the endoscope. The endoscope tube passes successively through the main tube 4 and the inner sheath to the surgical area for obtaining visibility of surgical area and performing procedures.

A method of using a percutaneous puncture and dilation visible irrigation-suction system comprises steps as below.

In the preoperative step, choosing a proper size sheath tube firstly according to different cases, wherein optional inner diameter of inner sheath ranges from Fr10-Fr20, while that of outer sheath ranges from Fr12-Fr26, and optional working length of out sheath ranges from 50-200 mm. Moreover, sheath tube can be changed immediately if required.

For example, an Fr14 outer sheath, Fr11 inner sheath and 60 mm working length sheath tube for percutaneous puncture tract dilation is used. In the percutaneous puncture and dilation step, performing precise orientation under the guidance of ultrasound, bedside fluoroscopy, or mobile C arm fluoroscopy, selecting 18-gauge needle for puncture into cavity of target organ, introducing guide wire via the needle, and then making a confirmation with radiography. After that, pulling out the needle, introducing an Fr14 puncture dilator over the guide wire for tract dilation. After removing the Fr14 puncture dilator, introducing an Fr14 outer diameter and 60 mm working length sheath tube into the lumen of target visceral organ over the guide wire to establish a percutaneous puncture tract. Then, inserting the endoscope system through the working channel of sheath tube, checking the puncture depth of free end of sheath tube on the monitor, and if not suitable, then adjustment could be made under fluoroscopic guidance.

In the assembling step for the percutaneous puncture and dilation irrigation-suction system, after completion of precise percutaneous puncture and dilation step, in the percutaneous puncture suction system presented in this invention, seamless connecting sheath main body and sheath base in the sheath tube with a positioning pin and then fixing them by a lock nut in the sheath tube. Then connecting an irrigation pump predetermined in safe irrigation pressure and flow to irrigation port 6 via a fluid inlet tube. After that, connecting suction tube 1, which is connected to the main tube 4, to a continuous controllable negative pressure suction system, and providing a tissue collecting bottle between suction tube 1 and the continuous controllable negative pressure suction system, and then covering a rubber sealing cap 2 on the endoscope inlet port 3.

In the endoscope system working step, connecting the endoscope system to camera light source firstly. Then, introducing laser fiber, lithotripter probe or electrode into the working channel 13.3 in the endoscope system. After that, opening the irrigation port 6, and turning on the irrigation pump, continuous controllable negative pressure suction aspirator, camera light source and treatment device. Then, inserting endoscope successively through the rubber sealing cap 2, endoscope inlet port 3, main tube 4 and the inner sheath of sheath tube, finally into the cavity of target organ. Thereinto, the irrigation fluid injected through the irrigation channel between inner and outer sheath of sheath tube would generate a multiple-orientation, vortex irrigation fluid in the cavity of target organ, which offers a clear visibility of surgical field. With the continuous controllable negative pressure suction aspirator and with controlling the negative pressure hole, the postoperative fluid containing all the substances after intraluminal procedure is efficiently one-way sucked out of body successively through inner sheath 10, sheath main body 5, suction tube 1 and suction rubber tube. During the whole procedure, sufficient irrigation combined with continuous controllable negative pressure suction together maintain safe low intraluminal pressure and clear visibility of surgical field, which thus achieves a safe, efficient and low cost procedure.

Finally, at the end of procedure, confirming there is no residual substance with the real-time imaging, withdrawing the endoscope, placing drainage tube through the guide wire, then removing the percutaneous puncture and dilation irrigation-suction system, and fixing the drainage tube. After that, finishing the procedure. For the favorable outcome in selected patients (no preoperative infection, no concurrent retrograde endoscopy and no visible bleeding), the procedure can be finished without any drainage tube or stent, such as tubeless or total tubeless super-mini percutaneous nephrolithotomy (SMP).

The above are merely the preferred embodiments of the present invention and the intention is not to limit the scope of the present invention. The present invention is intended to cover all changes, various modifications and equivalent arrangements included within the principle and scope of the present invention according to the technical essence of the present invention.

What is claimed is:

1. A visible percutaneous puncture and dilation irrigation-suction system comprising:
    a main tube having a proximal end and a distal end, the proximal end configured for insertion of an endoscope therethrough;
    a sheath tube having a proximal end and a distal end, the sheath tube comprises an inner sheath and an outer sheath, a proximal end of the sheath tube is attached to the distal end of the main tube such that the inner sheath and main tube form a contiguous channel configured for insertion of the endoscope therethrough;
    an irrigation port connected to the sheath tube, the irrigation port configured to allow fluid to be pumped from the irrigation port into a space between the inner sheath and outer sheath and exit through a fluid outlet opening at a distal end of the outer sheath into a surgical area;
    a suction tube connected to the main tube configured to aspirate substances from the surgical area through the contiguous channel; the suction tube is connected to a negative pressure valve and a negative pressure control hole is formed in the suction tube;
    the main tube and the inner sheath are coaxial, the main tube is connected to the sheath tube via a sheath body, and the irrigation port is arranged at a junction between the main tube and the sheath tube;
    the sheath body comprises a sheath main body connected to the main tube and a sheath base sleeved on the outer sheath, a guiding conical surface is provided at a joint part between the sheath base and the main tube, the main tube is mounted to the guiding conical surface, and the sheath main body and the sheath base are fixed by a lock nut.

2. The visible percutaneous puncture and dilation irrigation-suction system according to claim 1, wherein a merging area is designed at the distal end of the sheath tube, the merging area is embedded between the inner and outer sheath, the inner sheath and the outer sheath merge at the merging area.

3. The visible percutaneous puncture and dilation irrigation-suction system according to claim 2, wherein the fluid outlet opening in the distal end of sheath tube is designed in the merging area.

4. The visible percutaneous puncture and dilation irrigation-suction system according to claim 1, wherein the proximal end of the main tube is designed for inserting the endoscope, and the proximal end also has a receptacle covered with a rubber sealing cap.

5. The visible percutaneous puncture and dilation irrigation-suction system according to claim 1, wherein the endoscope comprises an endoscope body, an endoscope tube connected with the endoscope body, and an endoscope sheath which is sleeved on the endoscope tube and is fixedly secured to the endoscope body by a sheath lock, a working channel and an optical channel are provided inside the endoscope tube, the working channel is connected with an instrument inlet provided in the endoscope body, the optical channel is connected with an onicular lens group provided in the endoscope body, and an irrigation port of the endoscope is connected to the endoscope body.

6. The visible percutaneous puncture and dilation irrigation-suction system according to claim 5, wherein at least one fluid tube is welded to an external surface of the endoscope tube, the fluid tube is in parallel with the endoscope tube, a replenishing-irrigation port, which is connected to the fluid tube, is arranged on the endoscope body.

\* \* \* \* \*